(12) United States Patent
Lelievre et al.

(10) Patent No.: US 12,006,509 B2
(45) Date of Patent: Jun. 11, 2024

(54) MACROTUMOR ENGINEERING

(71) Applicant: Purdue Research Foundation, West Lafayette, IN (US)

(72) Inventors: Sophie Andree Lelievre, West Lafayette, IN (US); Rahim Rahimi, West Lafayette, IN (US); Tim Kwok, Philadelphia, PA (US)

(73) Assignee: Purdue Research Foundation, West Lafayette, IN (US)

( * ) Notice: Subject to any disclaimer, the term of this patent is extended or adjusted under 35 U.S.C. 154(b) by 620 days.

(21) Appl. No.: 16/896,278

(22) Filed: Jun. 9, 2020

(65) Prior Publication Data

US 2020/0399589 A1 Dec. 24, 2020

Related U.S. Application Data

(60) Provisional application No. 62/863,625, filed on Jun. 19, 2019.

(51) Int. Cl.
| | | |
|---|---|---|
| *C12N 5/00* | (2006.01) | |
| *C12M 1/12* | (2006.01) | |
| *C12N 5/09* | (2010.01) | |

(52) U.S. Cl.
CPC ........... *C12N 5/0068* (2013.01); *C12M 25/14* (2013.01); *C12N 5/0062* (2013.01); *C12N 5/0693* (2013.01); *C12N 2533/30* (2013.01); *C12N 2533/52* (2013.01); *C12N 2533/54* (2013.01); *C12N 2533/80* (2013.01)

(58) Field of Classification Search
CPC .. C12N 5/0068; C12N 5/0062; C12N 5/0693; C12N 2533/30; C12M 25/14
See application file for complete search history.

(56) References Cited

PUBLICATIONS

Teixeira et al., Evaluation of bone marrow stem cell response to PLA scaffolds manufactured by 3D printing and coated with polydopamine and type I collagen, Journal of Biomedical Materials Research Part B: Applied Biomaterials, 107B(1): 38-49. (Year: 2019).*
Bruzauskaite et al., Scaffolds and cells for tissue regeneration: different scaffold pore sizes—different cell effects, Cytotechnology: 68: 355-369. (Year: 2016).*
Aravamudhan et al., Micro-Nanostructures of Cellulose-Collagen for Critical Sized Bone Defect Healing, Macromolecular Bioscience, 18: 1700263-1700263. (Year: 2018).*
Gleeson et al., Additional of hydroxyapatite improves stiffness, interconnectivity and osteogenic potential of a highly porous collagen-based scaffold for bone tissue regeneration, European Cells and Materials, 20: 218-230. (Year: 2010).*
Sapp et al., Multilayer three-dimensional filter paper constructs for the culture and analysis of aortic valvular interstitial cells, Acta Biomaterialia, 13: 199-206. (Year: 2015).*
Fu et al., Spontaneous formation of tumor spheroid on a hydrophilic filter paper for cancer stem cell enrichment, Colloids and Surfaces B: Biointerfaces: 426-434. (Year: 2019).*
Millipore Sigma, Whatman qualitative filter paper, Grade 114, retrieved from internet Aug. 14, 2023. (Year: 2023).*
Ng et al., Paper-based cell culture platform and its emerging biomedical applications, Materials Today, 20(1): 32-44. (Year: 2017).*
Derda et al., Paper-supported 3D cell culture for tissue-based bioassays, PNAS, 106(44): 18457-18462. (Year: 2009).*

* cited by examiner

*Primary Examiner* — Laura Schuberg
*Assistant Examiner* — Joseph Paul Miano
(74) *Attorney, Agent, or Firm* — Purdue Research Foundation

(57) ABSTRACT

A collagen-fibronectin-based method enables the production of tumors of centimeter size with recognizable pathological traits. The method supports reproducing tumor heterogeneity with preinvasive and invasive phenotypes and stacking of tumor portions using a paper-scaffold with 80 μm-punched holes for larger nodule creation and easy separation of tumor portions for analysis. Macrotumors are convenient for testing drug delivery and therapeutic tools that necessitate a minimum tumor size relevant to in vivo.

13 Claims, 7 Drawing Sheets

MACROTUMOR ENGINEERING

CROSS-REFERENCE TO RELATED APPLICATION

The present application claims the priority benefit of U.S. Provisional Application No. 62/863,625, filed Jun. 19, 2019, and the content of which is hereby incorporated by reference in its entirety.

FIELD OF INVENTION

This disclosure provides an approach to make tumors of centimeter size within 10 days in vitro with characteristics similar to those pathologically recognized in real tumors of the carcinoma type. Particularly, using scaffolds to increase the tumor size by 5 mm for each scaffold and scaffolds permitting the separation of tumor portions for different analyses.

BACKGROUND

The formation of tumors with recognizable phenotype and architecture in the presence of exogenous extracellular matrix (ECM) demonstrates the importance of three-dimensional (3D) cell culture in basic and translational cancer research. However, standard 3D cell culture usually leads to small tumor nodules (less than 800 μm) over a 10-day culture period, which corresponds to structures that are below detectable tumor sizes in vivo. Hence, drug delivery and other therapeutic tools requiring centimeter size tumors cannot be optimally developed and reproducibly tested in vitro prior to costly in vivo assessment. Rare attempts to produce large tumors (44 mm$^3$) via aggregation of a high quantity of cells lead to extensive necrosis within hours, without proper cancerous architecture for these masses that do not represent physiologically relevant cancer models. Recent sophisticated and complex approaches for larger tumor production (millimeter size) making use of 3D printing are only accessible to laboratories possessing the machinery and skills to operate the printer.

There remains a need to produce tumors sizes over centimeter without complex machinery for easy analyses.

SUMMARY OF THE INVENTION

The present disclosure has provided a method to produce tumors of 0.5 to 1.5 cm in size without complex machinery and with paper-based scaffold enabling the separation of tumor portions for easy analysis.

These and other features, aspects and advantages of the present invention will become better understood with reference to the following figures, associated descriptions and claims.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Figure 1:
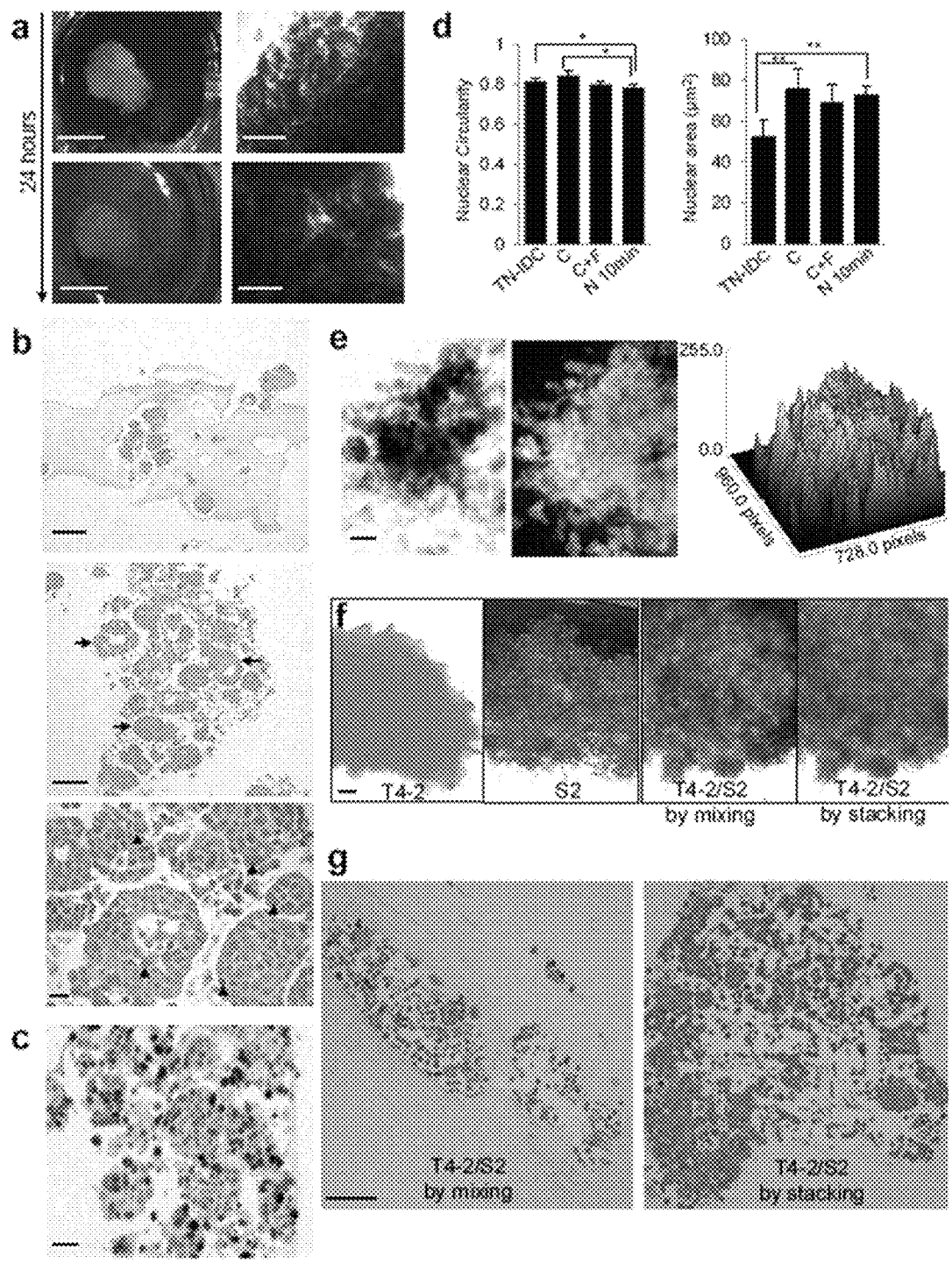
FIG. 1. Differential centrifugation of small tumor nodules leads to the formation of simple and mixed types of macrotumors with in vivo like pathological features. The formation of tumors of up to 600 μm in size was induced by culturing either IDC T4-2 cells or S2 DCIS cells in Matrigel™ drip culture for 10 days. Upon release from Matrigel™ with dispase treatment, tumor nodules were incubated with 100 μg/ml fibronectin solution, spun down either as a single type of nodules (9,000 nodules; a-e) or as mixed types of nodules (4,500 nodules of each tumor type; f-g) and embedded in collagen I (2,000 Pa) as detailed in the methods section. a. Pictures of a macrotumor formed by triple negative IDC T4-2 cells at time of preparation and 24 hours later, with 40× magnification in the right panels. b. H&E staining of sections of a 'control' culture (top image; nodules mixed in collagen without prior centrifugation and fixed after 10 minutes) and a macrotumor in collagen I after 24 h in culture, with pictures taken at low (middle image) and high (bottom image) magnifications. Arrows indicate nodule-like structures; arrowheads illustrate severe nuclear pleomorphism with some cells having small hyperchromatic nuclei and others having large nuclei with irregular shapes and prominent nucleoli, all features consistent with high-grade TN IDC. c. Immunohistochemistry for proliferation marker Ki67 (dark nuclear staining on H&E staining-black & white image) on a section of macrotumor IDC after 24 h of culture. d. Graphs of nuclear area (left) and circularity (right) of macrotumors prepared in collagen I with and without fibronectin at 24 and 72 hours of culture, and control nodules embedded in collagen I for 10 min without prior centrifugation, compared to triple negative (TN) IDC archival biopsy sections. e. Macrotumors cultured for 24 h were incubated with 17.25 μM doxorubicin for four hours and imaged with bright field and fluorescence microscopy (doxorubicin autofluorescence in the red channel). The surface plot displays the fluorescence signal throughout the imaged tumor region, indicating penetration of doxorubicin in all areas of the macrotumor. f. Fluorescence images of macrotumors formed by DiI-stained T4-2 nodules, CellMask™ Green-stained S2 nodules and mixed types of macrotumors with T4-2 and S2 nodules (either mixed before centrifugation 'T4-2/S2 by mixing' or sequentially centrifuged 'T4-2/S2 by stacking') taken with a Nikon®ECLIPSE® Ts2 inverted microscope (Nikon, Melville, NY). g. H&E stained sections of mixed types of tumors (black & white image). Size bars, 5 mm (A, left panel), 1 mm (A, right panel), 200 μm (F), 100 μm (B top and middle images; E, G), 50 μm (C), 25 μm (B, bottom image). In D, 50 nuclei analyzed in two biological replicates for macrotumors and 100 nuclei analyzed per section of three tissue samples; *P<0.05 **P<0.01; ANOVA with Tukey's posthoc test.
Figure 2:
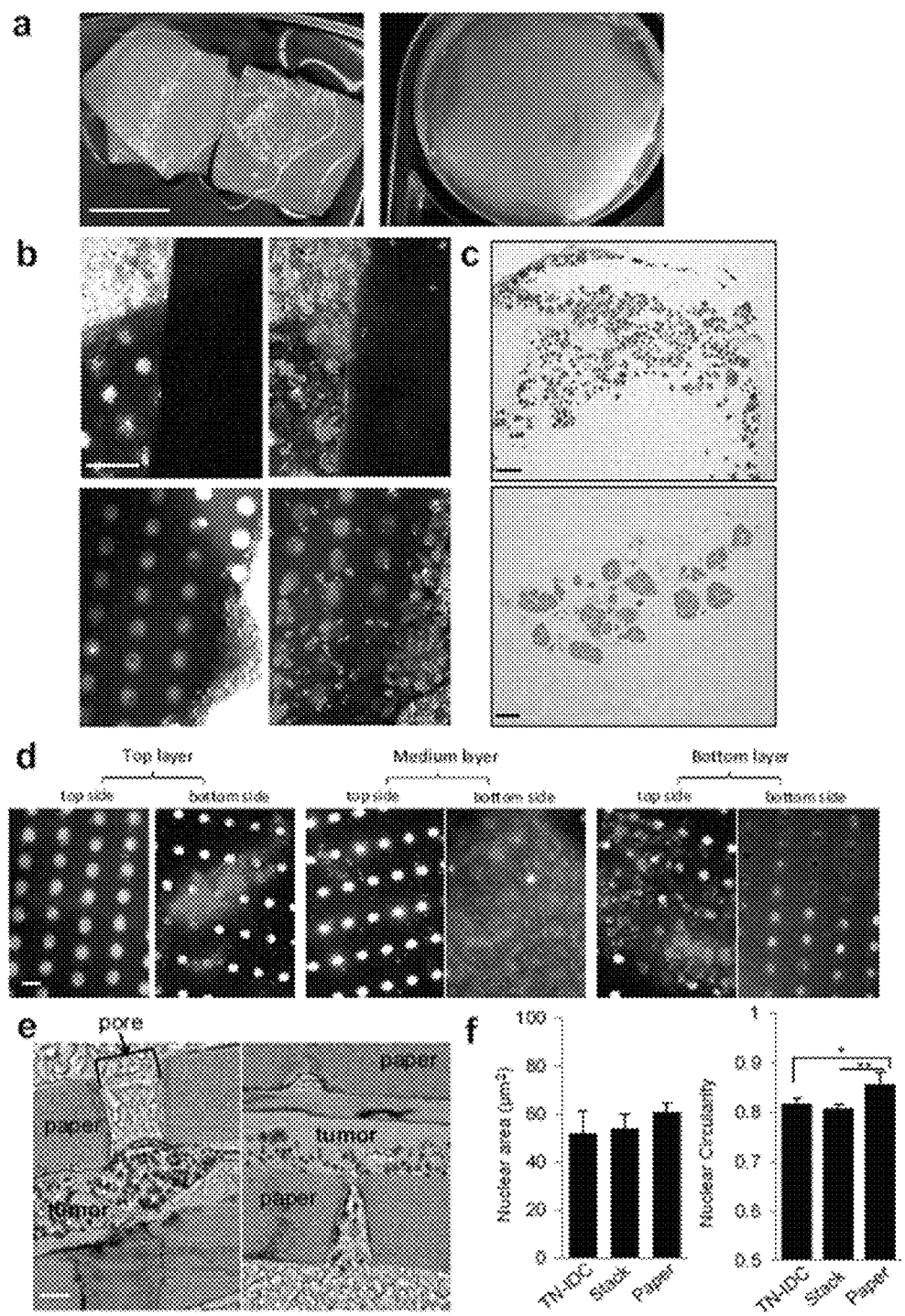
FIG. 2. Stacking method on cellulose acetate scaffold produces larger tumors that can be easily separated into portions for analysis. Macrotumors were prepared in fibronectin and covered with collagen I as described in the Materials and Method, but instead of resting on a collagen I-coated plastic surface, they were placed on cellulose acetate scaffold prewet in a solution of collagen I at 2,000 Pa. a. left: photograph of three scaffold in collagen solution used in one experiment. Scaffold are stacked at an angle to allow easy reach when they need to be separated. Right: DiI-stained macrotumor formed in a tri-stack model. b. Images of three stacked scaffolds with macrotumors for which scaffolds were alternatively stained with DiI or CellMask™ Bright-field images are focused on the holes (left) and fluorescence images are focused on the cells (right). c. H&E stained sections of macrotumor on paper scaffold at low (top) and high magnification (bottom). d. Peeling off the staked scaffold after 24 hours in culture and imaging of the macrotumor portions by fluorescence microscopy on each side of the scaffold. The scaffolds were initially stacked together so that nodules are on the top side of the bottom layer, the bottom side of the intermediate layer, and the bottom side of the top layer. e. bright field images of paper scaffolds with toluidine blue-stained cells (some seen inside the holes; arrows). f. Graphs of nuclear area (left) and circularity (right) of macrotumors prepared on cellulose acetate scaffold at 24 hours of culture compared to triple negative (TN)-IDC from archival biopsy section. Size bars, 5 mm (A), 500 μm (B), 200 μm (D), 100 μm (C), 50 μm (E). In F, 50 nuclei analyzed in two biological replicates for macrotumors and 100 nuclei analyzed per section of three tissue samples; *$P<0.05$ **$P<0.01$; ANOVA with Tukey's posthoc test.

Standard 3D culture of cancer cells in biological ECM such as Engelbreth-Holm-Swarm (EHS) and collagen I gels reveals recognizable pathological traits based on cellularity and nuclear morphometry, as demonstrated notably with breast cancers, the original models used to develop 3D cell culture. We reasoned that instead of forcing a high number of cells to form large but nonphenotypically relevant nodules, starting from phenotypically sound small tumors and clustering them together would maintain the organization of carcinomas. Indeed, 9000 tumor nodules formed by triple negative breast cancer HMT-3522 T4-2 cells, released from a 10-day Matrigel™-based culture, spun down, embedded in collagen I with a stiffness of 2000 Pa (Young's modulus) and cultured in a 1.9 cm$^2$ well, appeared without rapid and extended necrosis [cell survival, 94-96% at 24 h and 92% at 72 h based on trypan blue staining of tumor cells dissociated with trypsin] (FIG. 1a). Mixing matrix organizer fibronectin with collagen I improved cohesion, slightly raised ECM stiffness and tumor volume at 24 h compared to cells in culture only in collagen I (FIG. 1, b-c; Table 1). Upon paraffin-embedding and Hematoxylin & Eosin (H&E) staining, tumors with long axis and short axis of respective size ranges 62-94 mm and 43-84 mm, were classified as high-grade invasive ductal carcinomas (IDC) with numerous nodule-like structures of irregular shape and severe nuclear pleomorphism, high proliferation rate (Ki67 marker positive cells above 75%); FIG. 1b-c; Supplementary FIG. 1 d-e) and rare necrotic and apoptotic cells. Nuclear morphometry analysis revealed large and poorly circular nuclei confirming observations by pathologists. Importantly, macrotumors prepared by coating small tumor nodules with 100 μg/ml fibronectin prior to embedding in collagen I had nuclear morphometric parameters similar to those of real triple negative IDC (FIG. 1, d; Table 2-3). Macrotumors obtained with another TN IDC cell type, MDA-MB-231 were high grade TN IDC based on the strong degree of morphologic pleomorphism (cell size, nuclear size and shape) and the heterogeneity in the amount of cytoplasm; these tumors appeared less cohesive than those formed by T4-2 cells likely due to the known lack of E-cadherin expression in MDA-MB-231 cells (FIG. 2).

Figure 3:
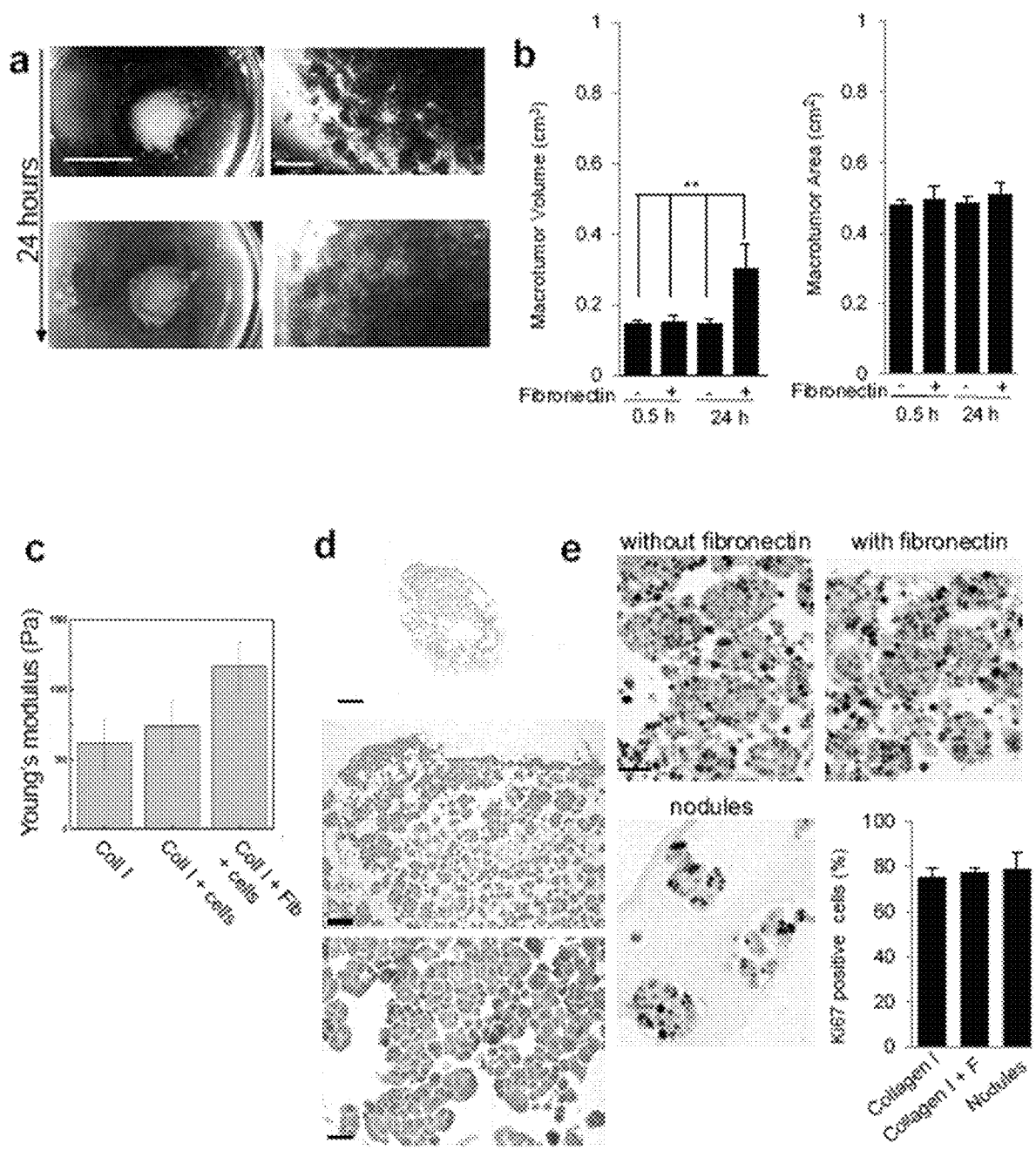
FIG. 3. Impact of fibronectin on macrotumors. Small tumors (9000) preformed in Matrigel™ for 10 days were used to make macrotumors as described in the Methods section with or without incubation with 100 μg/ml fibronectin. a. Macrotumors prepared without fibronectin incubation and cultured for 24 hours (right images at 40× magnification). b. Comparison of volumes and areas of macrotumors with (+) or without (−) incubation with fibronectin after 30 minutes (0.5 h) and 24 h of culture; n=5, mean+/−SEM. c. Stiffness of collagen I (Young's modulus, Pa) prepared with Collagen I, and measured with customized eXpert 4000, ADMET by constant pressure on unconstrained sample (see reference 15 for details for this procedure). d. Staining with H&E of macrotumors prepared without incubation with fibronectin. e. representative images of macrotumors and nodules (mixed in collagen I for 10 minutes without prior centrifugation). Shown is the bar graph of the percentage of cells positive for proliferation marker Ki67 staining after 24 h of culture of macrotumors in collagen I or collagen I+fibronectin (F), or nodules (mixed in collagen I for 10 minutes without prior centrifugation); n=2; 150 nuclei analyzed per biological replicate. Size bars, 5 mm (A, left panel), 1 mm (A, right panel), 500 μm (D, top image), 100 μm (D, middle image), 50 μm (E), 25 μm (D, bottom image). **$P<0.01$, ANOVA with Tukey's posthoc test FIG. 4. Macrotumor formed with MDA-MB-231 cells. a. picture of macrotumor after 24 h of culture. b. image of a portion of macrotumor after H&E staining. Size bars, 2 mm (A), 100 μm (B)

As further proof-of-principle we prepared macrotumors with Head & Neck HN31 cancer cells in collagen I of 2,000 Pa stiffness, that was pathologically classified as squamous cell carcinoma based on the presence of abundant eosinophilic cytoplasm and nuclear hyperchromasia (FIG. 3). The collagen I matrix gives the possibility of creating a stiffness appropriate for IDC (at least 2,000 Pa) compared to EHS gels (~800 Pa). Although placing tumor nodules in collagen of appropriate stiffness to form the macrotumor after EHS culture achieves an organization like in vivo (FIG. 1-b), culture can also be done from the beginning in collagen I of appropriate stiffness, followed by collagenase treatment and centrifugation of small tumor nodules prior to macrotumor formation in collagen I (FIG. 3).

Figure 4:
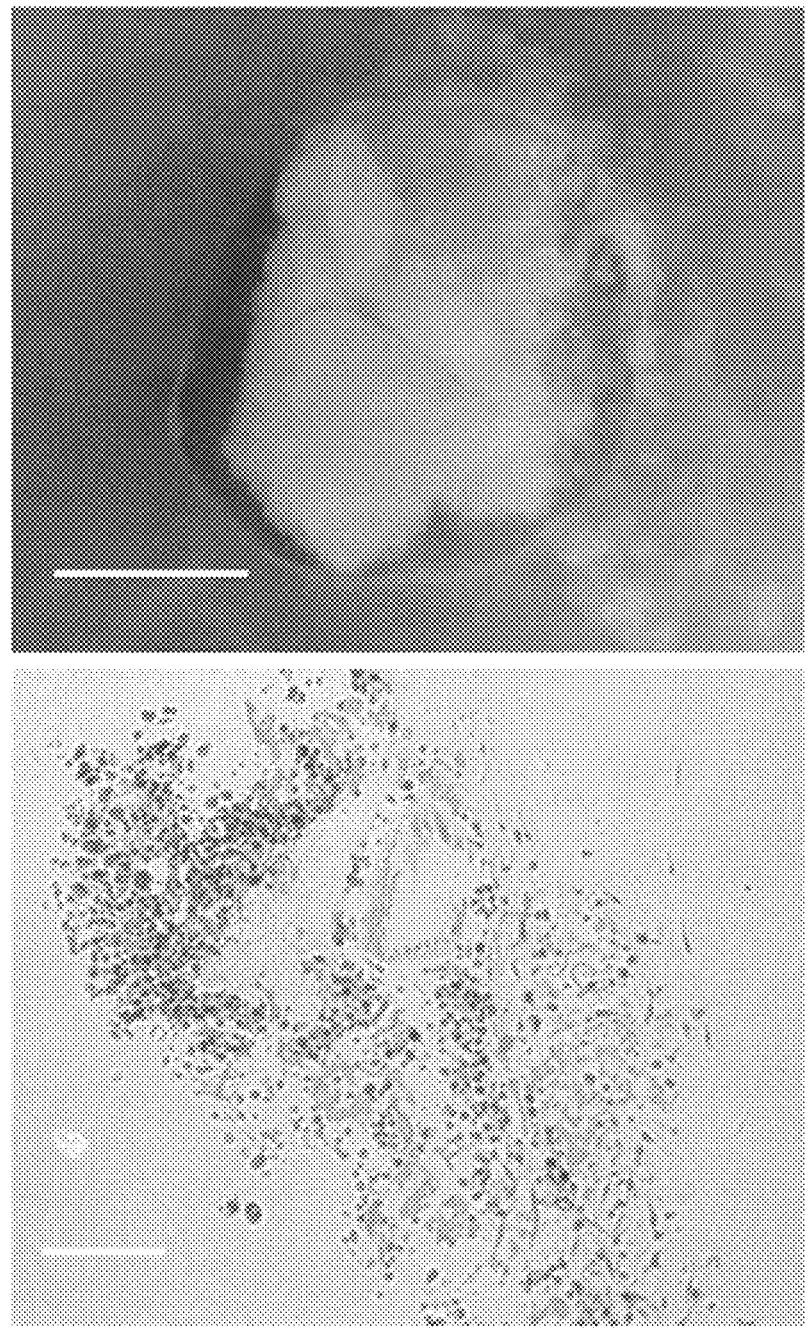

Upon a 4-h treatment of T4-2 cells with 10 μg/ml [17.25 μM] cytotoxic drug doxorubicin, the analysis of the drug's autoflorescence with confocal Z-sections showed that drug uptake occurred throughout the macrotumors, regardless of the location of the cells (FIG. 1-e). Treatment with doxorubicin (10 μM; 24 h) followed by a six-day resting period appeared to decrease tumor size after day 4 (FIG. 4), and macrotumors treated weekly (10 μM; 24 h) for three weeks were increasingly affected based on pathological assessment of their nuclear morphology at days 7 and 21.

Most tumors are heterogeneous not only because of cell features but also from a phenotypic standpoint, with portions that are noninvasive (ductal carcinoma in situ [DCIS]-like) and invasive (IDC-like). Such heterogeneity leading to mixed types of tumor influences the risk of cancer progression and treatment response. Using a similar approach as for the single cell type of macrotumors, we mixed equal amounts of nodules preformed in Matrigel™ by DiI-stained IDC T4-2 cells and T4-2 precursor, CellMask™ Green-stained DCIS S2 cells, either at once or via sequential centrifugations (first T4-2 nodules, then S2 nodules on top of the pellet of T4-2 nodules), before embedding in collagen I. After 24 h of culture, the distribution of nodular structures reflected the preparation steps for the mixed type of macrotumor (either a mixture of nodules of different types or clearly separate regions of IDC and DCIS nodular structures) (FIG. 1-f). A pathologist blinded to the sample type distinguished H&E-stained tumors with more than one population of cells compared to tumors formed by one population of cells. Mixed tumors formed by stepwise centrifugation had an overall heterogenous population of cells (from small to large), with irregular nuclei containing prominent nucleoli in large cells and hyperchromatic nuclei in small cells. Larger groups of cells displayed a more aggressive behavior (e.g., irregular extensions) and there were no 'intact' small tumor nodules. The mixed type of tumor formed by mixing IDC and DCIS nodules had nuclear shapes less irregular than in the tumors formed with the stepwise centrifugation (FIG. 1-g; Table 4). Overall, tumors formed by step-wise centrifugation of IDC and DCIS nodules were classified as mixed types with greater component (or percentage) of invasive carcinoma and lesser component (or percentage) of DCIS, and tumors formed by direct mixing of IDC and DCIS nodules were classified as mixed types with more extensive DCIS component than the invasive component, suggesting that the method used to produce the mixed type of macrotumor, although initially prepared with a similar number of IDC and DCIS nodules, determines pathological traits.

Figure 5:
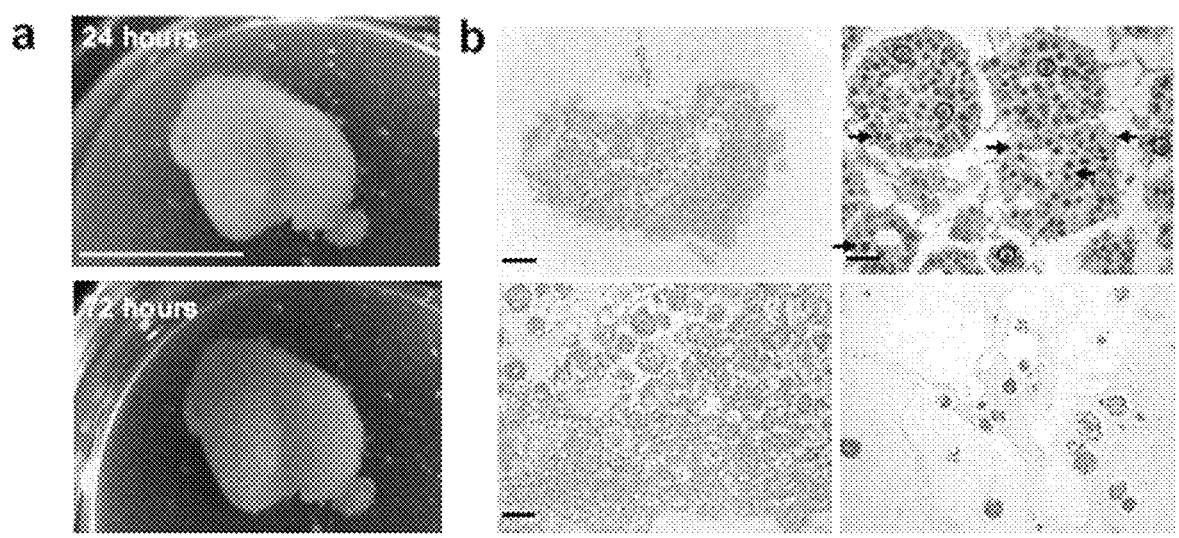
FIG. 5. Macrotumors formed by Head & Neck cancer HN31 cells. a. Images of a macrotumor at 24 and 72 h of culture. b. Top: Sections of a macrotumor after 24 hours of culture (different sample compared to A); indications of cells with abundant eosinophilic cytoplasm (arrows) and hyperchromatic nuclei (circles) that are characteristic features of squamous cells carcinoma (right image). Bottom: macrotumor (left) and nodules embedded in collagen I for 10 minutes without prior centrifugation. Size bars, 5 mm (A), 500 μm (B top left), 100 μm (B, bottom), 25 μm (B, right)
Figure 6:
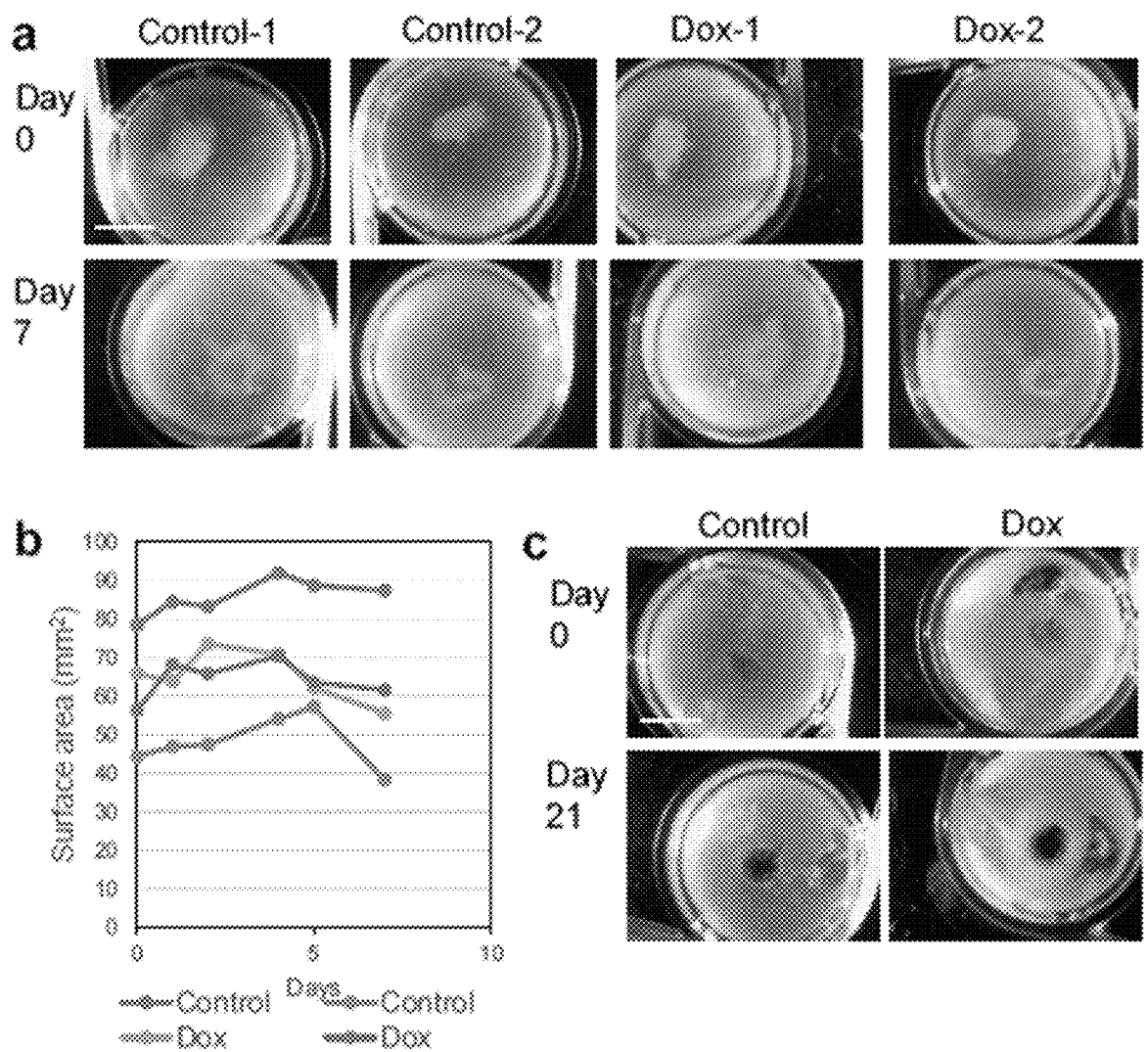
FIG. 6. Effect of Doxorubicin treatment on macrotumors formed by T4-2 cells. a. Images of macrotumors treated (Dox) or untreated (Control) with 10 μM doxorubicin at day 0, for 24 hours and further cultured for six days. n=two replicates for this experiment (1, 2). b. Shown are the surface areas of macrotumors from A measured at days 0, 1, 2, 4, 5, and 7. c. Another experiment with 24 h Doxorubicin (Dox) treatment at day 0, 7 and 14 with images taken at day 0 and 21. Size bars, 5 mm FIG. 7. Macrotumor prepared by scaffold stacking. a. Three 1×1 cm scaffolds of cellulose acetate with 100 μm holes every 200 μm soaked in ice-cold collagen I solution (2,000 Pa). The inset shows an enlarged area of the scaffold with distinct pores. b. stacked scaffolds assembled at an angle from each other to make corners apparent for easy reach. c. Black & White images of H&E stained stacked macrotumors after 24 hours of culture, with enlargement of a region going through a hole (see inset with arrow). Size bars, 200 μm (C, left), 100 μm (C, right)
Figure 7:
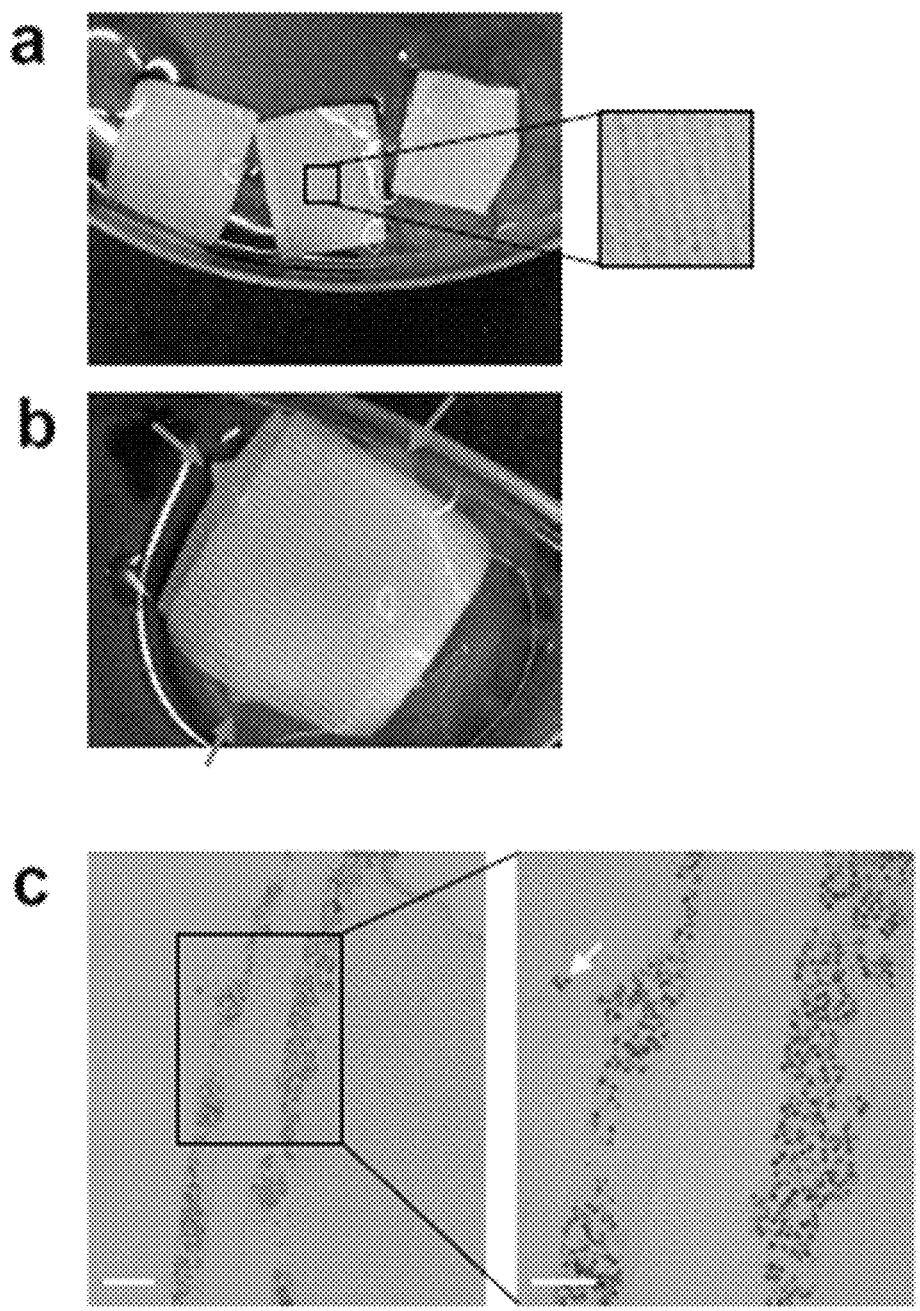

To produce even bigger tumors permitting various analyses, we designed a multilayer stacking procedure of macrotumors cultured on porous, cell culture-amenable cellulose acetate membranes (1 cm$^2$) that were prewet in collagen I solution (see Methods). To increase sensing between layers and morphological changes within the macrotumor, the membranes were laser micromachined with pores at an average diameter of ~80 μm and density of ~4 pores/mm$^2$ (FIG. 2-a, and FIG. 5-a). Three scaffolds were stacked together for a macrotumor height of 1.5 cm. Each tumor-bearing scaffold in the stack was alternatively stained with live dye (DiI or CellMask™ (Green)) prior to assembly (FIG. 2b-c). Each scaffold could be easily peeled off, with cells remaining on their corresponding scaffold as shown with fluorescence microscopy at days 1 and 5 of culture. As expected cohesive areas of cells were also seen on the sides of the scaffold and through the holes, which was confirmed after paraffin-embedding and H&E staining of the stacked macrotumor (FIG. 2-b, d, e; FIG. 5-b, c). The stacked macrotumors showed average nuclear morphometry (circularity and area) not significantly different from the average morphometry measured in real TN IDC (FIG. 2f).

In conclusion, our method provides a simple, yet effective approach to create centimeter size tumor nodules that maintain a recognizable pathological signature. It is amenable to the formation of preinvasive and invasive tumors that present nodular structures as it is the case for carcinomas, the most extensive type of human cancers. The engineering aspect of the stackable culture can also be reproduced in most research settings. The fact that a stack can be separated after a few days of culture is due to the preparation of separate tumor portions via collagen embedding, yet it does not prevent tumor reorganization with time as in vivo (FIG. 2c). The possibility of separating stacks would permit various analyses of the same macrotumor with enough quantities of tissue not only for embedding and sectioning for immunolabeling but also for extractions and measurement of proteins, RNAs, DNA, etc. In vivo mimicry may be further extended by mixing nodules with fibroblasts or immune cells before adding collagen I to form the macrotumor. As it currently stands the macrotumor method would benefit most applications related to drug development and testing, including drug delivery system, like slow release gels, and other methods to treat cancer cells with nanoparticles, nanotubes and microdevices (e.g., electrodes) that depend on tumor size and require definite in vivo-like models.

TABLE 1

Size measurement of macrotumors embedded in collagen I with or without fibronectin pretreatment of tumor nodules and after 30 minutes (0.5 h) and 24 hours in culture. Five tumors were measured in each group (biological replicates).

|  | No fibronectin | Fibronectin |
| --- | --- | --- |
| Long axis (L; cm) range | | |
| 0.5 h | 0.75-0.89 | 0.64-0.94 |
| 24 h | 0.64-0.90 | 0.62-0.94 |
| Short axis (S; cm) range | | |
| 0.5 h | 0.55-0.70 | 0.43-0.84 |
| 24 h | 0.51-0.77 | 0.49-0.79 |
| Volume (L × S × S)$^+$ (cm$^3$) | | |
| 0.5 h | 0.145 ± 0.35 | 0.148 ± 0.08 |
| 24 h | 0.145 ± 0.65 | 0.299 ± 0.30 |
| Area (L × S) (cm$^2$) | | |
| 0.5 h | 0.48 ± 0.07 | 0.50 ± 0.18 |
| 24 h | 0.49 ± 0.10 | 0.51 ± 0.16 |

Mean +/− SD;

$^+$formula used for xenografts

TABLE 2

Pathological assessment (1) blinded to the nature of the samples of T4-2 cells in culture. Minimal or low = 1; moderate = 2; severe or high = 3); Irreg. = irregular; spher. = spherical; nod. = nodules. E = experiment; N = nodules mixed in collagen I and fixed after 10 minutes; C = centrifugation of nodules before embedding in collagen I- 24 hours of culture; E = experiment (all E with same number were done with the same batch of cells and at the same time); F = centrifugation of nodules incubated with fibronectin before embedding in collagen I- 24 hours of culture; P = centrifugation of nodules incubated with fibronectin before embedding in collagen I on paper scaffold-24 hours of culture. The number after F, C or P correspond to a technical replicate in that particular experiment (i.e., a distinct 3D culture preparation). DCIS vs. IDC final impression based on (1) shape and sphericity and (2) presence and extent of dissociated cells (indicator of invasion when infiltration of stroma). All neoplasias are considered high grade.

| Sample | E4N | E6N1 | E3C1 | E5C2 | E5C3 | E3F2 | E5F2 | E5F3 | paper E6 |
|---|---|---|---|---|---|---|---|---|---|
| Homogeneity In nodule size | 1 | 1 | 1 | 1 | 1 | 1 | 1 | 1 | 1 |
| Overall cellularity | 3 | 2 | 2 | 3 | 3 | 3 | 3 | 3 | 1 |
| Homogeneity of shape | 1 | 2 | 1 | 1 | 1 | 1 | 1 | 1 | 1 |
| Sphericity | 1 | 2-3 | 1 | 1 | 1 | 1 | 1 | 2 | 1 |
| Shape (round/spherical) | Irreg. | Spher. with extensions | Rare round nod. | Rare round nod. | Small irreg. clusters | Rare round nod. | Irreg. | Irreg. | Irreg. |
| Budding | 3 | 1 | 2 | 1 | 3 | 2 | 1 | 2 | 0-1 |
| Nuclear pleomorphism | 3 | 3 | 3 | 2 | 3 | 3 | 3 | 3 | 3 |
| Mitoses | 3 | 1 |  | 1 |  | 1 | 3 | 2 | 1 |
| Dissociated cells | 3 | 1 | 1 | 2 | 2 | 3 | 3 | 2 | 1 |
| Necrosis | 0 | 0 | Single cell | Single cell | 0 | Single cell | Single cell | Single cell | 0 |
| DCIS vs IDC | IDC | DCIS | IDC | IDC | IDC | IDC | IDC | IDC | IDC |

Note:
Pathologist from Human medicine expert in breast neoplasia.

TABLE 3

Pathological assessment (2) blinded to the nature of the samples of T4-2 cells in culture. E = experiment; N = nodules mixed in collagen I and fixed after 10 minutes; C = centrifugation of nodules before embedding in collagen I- 24 hours of culture; E = experiment (all E with same number were done with the same batch of cells and at the same time); F = centrifugation of nodules incubated with fibronectin before embedding in collagen I-24 hours of culture; P = centrifugation of nodules incubated with fibronectin before embedding in collagen I on paper scaffold-24 hours of culture. The number after F, C or P correspond to a technical replicate in that particular experiment (i.e., a distinct 3D culture preparation).

E6N1   Roughly spherical clusters of cohesive, polygonal neoplastic cells are widely distributed on a lawn of dense eosinophilic material. Neoplastic cells are cohesive with 1-4 nuclei and multiple nucleoli. Occasionally, there is a clear zone surrounding the cell nuclei.

E3C1   Polygonal to round neoplastic cells are arranged in multiple small clusters; however, many cells lack cohesiveness and show evidence of necrosis or apoptosis. Neoplastic cells contain 1-4 nuclei and a single eosinophilic inclusion body.

E5C2   Polygonal neoplastic cells are arranged in a small cluster, composed of approximately 30 round-to-polygonal cells with 1-2 nuclei, 2-5 nucleoli. A single cell is observed within a cellular lumen, suggestive of vascular mimicry.

E5C3   Neoplastic cells are arranged in irregular clusters and are cohesive, multifocally. Cells are polygonal to spherical and contain 1-10 nuclei, 1-4 nucleoli, and an abundant eosinophilic cytoplasm. Occasionally, cells appear apoptotic with hypereosinophilic cytoplasm and rounded, basophilic nuclei. Few neoplastic cells engulf small, but viable cells.

E3F1   Neoplastic cells are arranged in indistinct clusters. These cells lack distinct cellular boarders and some cells are separated by wispy basophilic material. Neoplastic cells have 1-5 nuclei, and a dense eosinophilic nucleolus. Occasionally 5-10 cells form an acinus, surrounding clear space.

E5F2   Neoplastic cells are loosely arranged in a misshapen cluster. Multifocally, cells along the periphery are polygonal with 1-2 nuclei and a basophilic nucleolus. The remaining cells along the periphery and within the center of the cluster are apoptotic with hypereosinophilic cytoplasm and shrunken nucleus.

E5F3   Cohesive neoplastic cells are arranged in three large cellular clusters. These cells are polygonal, but some cells are 25 μm in maximum diameter and contain up to ten nuclei. There is abundant clear space between cells. Rarely, viable neoplastic cells appear to engulf apoptotic cells. Few scattered apoptotic cells with hypereosinophilic cytoplasm and shrunken nuclei are identified throughout the section.

TABLE 3-continued

Pathological assessment (2) blinded to the nature of the samples of T4-2 cells in culture. E = experiment; N = nodules mixed in collagen I and fixed after 10 minutes; C = centrifugation of nodules before embedding in collagen I- 24 hours of culture; E = experiment (all E with same number were done with the same batch of cells and at the same time); F = centrifugation of nodules incubated with fibronectin before embedding in collagen I-24 hours of culture; P = centrifugation of nodules incubated with fibronectin before embedding in collagen I on paper scaffold-24 hours of culture. The number after F, C or P correspond to a technical replicate in that particular experiment (i.e., a distinct 3D culture preparation).

| | |
|---|---|
| E6P2 | Small clusters of polygonal cells with 2-4 nuclei/cell and single to multiple nucleoli. Each neoplastic cell contains abundant eosinophilic cytoplasm, and cellular arrangement is suggestive of intercellular bridging. |

Note:
Veterinary pathologist working on human and animal cancers.

TABLE 4

Pathological assessment (1) blinded to the nature of the samples for the mixed type of tumor experiments. A pathologist was asked to compare H&E stained sections of macrotumors in three coded samples and to also give a general observation of the cell population and finally to propose whether the macrotumor resulted from one cell type in culture or more than one cell type in culture (see italics). Samples are as it follows for experiment 9 (E9): S2 (technical replicate 2 of monoculture of S2 DCIS cells), M1 (technical replicate 1 of coculture of IDC T4-2 cells and DCIS S2 cells with preformed small nodules mixed before centrifugation and embedding in collagen I), E2 (technical replicate 2 of coculture of IDC T4-2 cells and DCIS S2 cells with preformed small nodules spun down sequentially before embedding in collagen I).

| SAMPLE | Overall population | nuclei |
|---|---|---|
| E9S2 | Small clusters of cells but no acinar structures seen<br>Less heterogeneous than E2 sample<br>Cells with less cytoplasm than those in E2 sample<br>Maybe a rare mitotic figure<br>*Single population of cells favored* | Smaller than those in E2 sample<br>More round (less irregular) than those in E2 sample<br>Nucleoli less prominent than in E2 sample |
| E9M1 | More heterogeneity than in S2 sample<br>There are scattered small cells that look like normal mammary epithelial cells<br>*More than one population of cells favored* | Larger than those in S2<br>Shape is generally round (less irregular than in both S2 and E2 samples) |
| E9E2 | No intact tumor nodules seen<br>Heterogeneous: ranging from small to large cells<br>Small cells with less cytoplasm than the larger cells (cytoplasm abundant in some of these cells)<br>Larger groups of cells with irregular extensions (suggesting more aggressive behavior)<br>Only few mitotic figures<br>Some of the groups or larger cells appear to form microlumens<br>*More than one population of cells favored* | Small and hyperchromatic in small cells<br>Larger and more irregular in the larger cells compared to smaller cells<br>Larger nuclei have prominent nucleoli |

In one embodiment, the present disclosure provides a multilayer stacking for culturing macrotumors, wherein the multilayer stacking comprises a plurality of cell culture amenable substrates, wherein each substrate has a plurality of pores with a diameter of 60-100 μm, wherein the density of the pores on each substrate is 2-8 pores/mm², and wherein each substrate is pre-coated with a solution comprising one or more extracellular matrix.

In one embodiment of the present disclosure regarding the multilayer stacking, wherein the multilayer stacking comprises 2-4 cell culture amenable substrates.

In one embodiment of the present disclosure regarding the multilayer stacking, wherein said cell culture amenable substrate comprises polymeric material.

In one embodiment of the present disclosure regarding the multilayer stacking, wherein the polymeric material is cellulose acetate, polystyrene, polyurethane, polytetrafluoroethylene (PTFE), polyvinylchloride, polycarbonate, SU-8, or any combination thereof.

In one embodiment of the present disclosure regarding the multilayer stacking, wherein the multilayer stacking has a stiffness of 500-8,000 Pa if measured by indentation of unconstrained samples.

In one embodiment of the present disclosure regarding the multilayer stacking, wherein said one or more extracellular matrix is collagen I, fibronectin, collagen III, collagen IV, laminins, hyaluronic acid, heparan sulfate proteoglycan, or a combination thereof.

In one embodiment, the present disclosure presents a method of preparing a microtumor, wherein the method comprises:
  a) providing a pellet comprising a plurality of microtumors of 50-800 microns;
  b) providing a first cell culture amenable substrate, wherein the first substrate has a plurality of pores with a diameter of 60-100 µm, wherein the density of the pores on each substrate is 2-8 pores/mm$^2$, and the first substrate is pre-coated with a solution comprising one or more extracellular matrix, and depositing the pellet comprising a plurality of microtumors onto the first cell culture amenable substrate;
  c) adding an extracellular matrix solution onto the pellet deposited on the first substrate to allow the pellet to be embedded by the extracellular matrix solution;
  d) providing a second cell culture amenable substrate, wherein the second substrate has a plurality of pores with a diameter of 60-100 µm, wherein the density of the pores on each substrate is 2-8 pores/mm$^2$, and the second substrate is pre-coated with a solution comprising one or more extracellular matrix, and placing the second cell culture amenable substrate onto the extracellular matrix embedded microtumors deposited on the first cell culture amenable substrate;
  e) adding a solution comprising one or more extracellular matrix solution onto the pellet of deposited on the second substrate to allow the pellet to be embedded by the extracellular matrix solution;
  f) optionally repeating steps a)-e) to provide a total of 2-5 cell culture amenable substrates, wherein one pellet comprising a plurality of microtumors is deposited between two adjacent substrates;
  g) incubating the obtained multilayer stacking in a cell culture medium.

In one embodiment of the present disclosure regarding the method of preparing a macrotumor, wherein microtumors can be same or different microtumors to provide homogeneous or heterogeneous macrotumors.

In one embodiment of the present disclosure regarding the method of preparing a macrotumor, wherein microtumors may be from cells representing different carcinomas.

In one embodiment of the present disclosure regarding the method of preparing a macrotumor, wherein said one or more extracellular matrix is collagen I, fibronectin, collagen III, collagen IV, laminins, hyaluronic acid, heparan sulfate proteoglycan, or a combination thereof.

Methods
Cell Culture

The cell culture procedure to produce macrotumors is detailed in the online methods. HMT-3522 T4-2 and S2 cells and MDA-MB-231 cells were kept in culture in flasks for a maximum of 10 passages, with set seeding concentration of 11,700 cells/cm$^2$ and in H14 medium (serum-free DMDM/F12 medium [ThermoFisher Scientific, Waltham, MA] supplemented with 5 µg/ml (or 0.15 IU/ml) prolactin, 250 ng/ml insulin, 1.4 µM hydrocortisone, 0.1 nM β-estradiol, 2.6 ng/ml sodium selenite, 10 m/ml transferrin as previously detailed). For 3D drip culture in Matrigel™ (Corning Inc., Valparaiso, IN), seeding was 17,400 cells/cm$^2$ on a gel coat of 42 µl/cm$^2$ and with 5% final EHS gel concentration in the cell culture medium as previously detailed. After 10 days of culture tumor nodules were released by 30 min incubation at 37° C. with 0.75 ml of dispase (50 U/ml, BD Biosciences) per ml of EHS gel, followed by four washes in cell culture medium as previously detailed, before seeding the nodules for macrotumor formation. HN31 cells were cultured in DMEM medium supplemented with 10% fetal calf serum (ThermoFisher Scientific), at initial seeding concentration of 2000 cells/cm$^2$ for up to 10 passages. For 3D culture, 65000 HN31 cells were embedded in 300 µl collagen I (Advanced Matrix, Carlsbad, CA) prepared at 2000 Pa (according to the manufacturer's instructions) and deposited on a thin gel coat of 10.5 µl/cm$^2$ for each well of a 4-well plate as per a procedure detailed elsewhere. After 10 days of culture tumor nodules were released from collagen I with collagenase (Advanced Biomatrix Inc., San Diego CA). Briefly, cells are incubated with 78 µl/cm$^2$ of collagenase for 45-60 min at 37° C. and washed four times in cell culture medium as previously detailed, before seeding the nodules for the macrotumor preparation. An average of 9000 nodules was used for each macrotumor. The generation of a macrotumor was performed by centrifugation of tumor nodules prior to 20 minutes incubation with 100 µg/ml fibronectin (ThermoFisher Scientific; stock diluted 1/10 in H14 medium) followed by pellet covering with collagen I at the selected stiffness degree. Coculture was performed with T4-2 and S2 nodules prepared in Matrigel™ as above; nodules were mixed 1:1 (4,500 nodules for each cell type) either at once prior to centrifugation or in a stepwise manner prior to addition of collagen I. Culture on the cellulose acetate scaffold was performed by depositing the macrotumor, prepared as above, on a 1 cm$^2$ paper prewet in collagen I solution (on ice) for five seconds. Three scaffolds were placed on top of each other at an angle for each layer. The macrotumor was then covered with collagen I. For certain experiments tumor nodules were incubated for 30 min at 37° C. with CellMask™ Green Plasma Membrane Stain (50 µg/ml; Thermo Fisher Scientific), as it was used for S2 nodules, or with DiI (50 µg/ml; ThermoFisher Scientific), as it was used for T4-2 nodules, followed by three washes with 300 µl of H14 cell culture medium with a centrifugation step at 350 g for 5 min between each wash, prior to fibronectin treatment used in the stepwise preparation of the macrotumors (see online methods for step-by-step instructions).

Stiffness Measurement

The elastic modulus of cultured samples can be calculated from engineered stress-strains curve attained with compression tests. Uniaxial unconfined compression tests were performed using a standard universal testing machine (eXpert 4000, ADMET). Cylindrical samples were prepared by polymerizing collagen I (Advanced Matrix) according to the manufacturer's instructions in standard 4-well cell culture plates. The final diameter of the sample was 15 mm with a height of 2.8 mm, and all compression tests were carried out at a constant rate of 6 mm/min at room temperature.

Staining of Macrotumor Sections

Macrotumors were fixed in 4% paraformaldehyde (Santa Cruz; Dallas, TX) prior to embedding in paraffin at the Histology Research Laboratory, Department of Comparative Pathobiology, Purdue University, according to standard protocols used for tumor sample embedding, sectioning, immunohistochemistry with polyclonal antibodies against caspase 3 (1/200; Cell Signaling Tech, Danvers, MA) and Ki67 (1/500; Millipore-Sigma, St Louis, MO) and hematoxylin & eosin (H&E) staining. Certain sections were stained with toluidine blue (SigmaAldrich, St. Louis, MO) before H&E staining.

Microscopy and Image Analysis

Fluorescence images were acquired by a spinning-disk confocal microscope Andor Revolution XD (Andor Technology, South Windsor, CT) on the base of Olympus IX-71 inverted optical microscope with a 10× objective. Cell-Mask™ Green Plasma Membrane Stain, DiI dye and doxorubicin were excited by 488 nm, 561 nm, and 561 nm lasers, respectively. The emission signals were separated by 525/30 nm and 607/36 nm filters and recorded by iXon 888BV EMCCD camera (Andor Technology). The spacing between the optical sections was 1 μm and the number of sections was 80-100. The X-Y size of the acquired images was 665×665 Images were analyzed by Andor IQ software. The 3D-views were rendered from the z-stacks of the optical section images, and then movies (Supplementary Movies S1-S4) were recorded for a 360°-rotation of the 3D-views.

Images of macrotumors with H&E staining or fluorescently stained were recorded with a Nikon® Eclipse® Ti-E Microscope and a Nikon® Eclipse® Ti2 inverted microscope, respectively with 10× (numerical aperture 0.25) and 40× (numerical aperture 0.65) objectives.

Nuclear circularity and area measurements were done on H&E stained sections of macrotumors with the ImageJ software (imagej[dot]nih[dot]giv/ij) by outlining the nuclear shape as previously described. Sections from archival IDC biopsies were used under Purdue University IRB exemption approval #0502000712.

Images of whole tumors in culture and of paper scaffold were taken with a Plugable USB 2.0 Digital Microscope (Plugable Technologies, Redmond, WA). Tumor size (short and long axis) was measured with ImageJ. For pathological assessment slides were either directly visualized by microscopy or scanned (20× objective) with an Aperio/Pathology Slide Scanner (Leica Biosystems Inc., Buffalo Grove, IL).

Preparation of the Cellulose Acetate Scaffold

Holes were micromachined on cellulose acetate paper (Sartorius stedim, Goettingen Germany) at an average diameter of ~80 μm and density of ~4 pores/mm$^2$ using a laser engraver system (Universal Laser Systems, Inc., Scottsdale, AZ). Cellulose acetate-based membranes were laser-cut to 1.0 cm$^2$ scaffolds.

Statistical Analysis

All data are presented as average+/−standard deviation unless stated overwise (see Supplementary FIG. 1b). Comparison of multiple conditions (>2) was done with ANOVA and posthoc Tukey test. P<0.05 was considered significant.

Step-by-Step Protocol for the Preparation of Macrotumors

A. Preparation of Small Breast Tumor Nodules with Triple Negative T4-2 Cells

Detailed protocols to handle the HMT 3522 T4-2 cells and for the standard Matrigel™ drip culture can be found in previously published articles.

1. Coat the bottom surface of each well of a 4-well plate with 105 μl of Matrigel™ (Corning) nanohub[dot]org/resources/25058/supportingdocs). Incubate at 37° C. for 15 minutes for the gel to solidify.
2. Detach the cells from their culture flask with trypsin-EDTA and prepare the cell suspension for cell counting.
3. Spin down the necessary quantity of cells for the number of wells sought (here six wells to obtain ~9,000 nodules) at 350 g for 5 min; seed 42,500 cells/well in a 4-well plate.
4. Resuspend the cells in 15011.1 of H14 medium and add drop-by-drop all over the 42 μl/cm$^2$ Matrigel™ coat of the well (nanohub[dot]org/resources/25058/supportingdocs). Let the cells rest in the hood. (Note that for cell culture we use serum free medium with additives of known concentrations; this type of medium is preferred when working with drug testing to ensure reproducibility, which would be a challenge otherwise with the many unknown parameters in serum).
5. After five minutes add 150 μl of H14 medium containing 10% Matrigel™ (135 μl medium+15 μlMatrigel™) drop-by-drop on top of the cells and place the plate, without shaking, in the cell culture incubator.
6. Change the medium (freshly mixed with additives) every other day.
7. At day 10 of culture, remove the cell culture medium and add 300 μl of dispase to each well such that it comes in direct contact with the gel. Incubate at 37° C. for 45 minutes to one hour so that the gel is dissolved.
8. Collect the nodules and centrifuge at 350 g for 5 min to remove the dispase.
9. Discard the supernatant and wash with 300 μl DMEM/F12 without mixing with the pipette tip—repeat this wash and centrifugation step three times.
10. Resuspend the nodules carefully in 0.5 ml of H14 medium; gather nodules from six wells of 4-well plates maximum with that initial volume of medium. If more wells are needed for the experiments, proceed with another 0.5 ml of medium for up to six wells from which to gather nodules, etc.

Note: The preparation of the small tumor nodules can also be done in collagen I followed by removal with collagenase (see general materials and methods and previously published detailed instructions).

B. Procedure for the Generation of Macrotumors in Culture

1. Aliquot 0.5 ml of nodules from six wells of 4-well plates into Eppendorf tubes (see Section A step #10).
1. Collect nodules by centrifugation at 350 g for 5 min at room temperature.
2. Remove the supernatant.
3. Add 10 μl of fibronectin (1 mg/ml solution prepared according to the manufacturer's instructions in distilled water; ThermoFisher Scientific) and move the pellet up-and-down in the pipet tip once to break it.
4. Keep the solution for 1 min without further mixing.
5. Add 90 μl of medium slowly against the inner sidewall of the tube to reach 100 μg/ml.
6. Incubate the Eppendorf tube containing the tumor nodules at 37° C. for 20 min.
7. Centrifuge at 300 g for 1 min at room temperature.
8. Remove the medium by aspiration (vacuum tube).
9. Add 200 μl of cell culture medium slowly against the inner wall of the Eppendorf tube, but do not break the pellet of nodules.
10. Transfer the solution containing the pellet of nodules with a large-bore 1 ml pipette tip to one well of a 4-well plate precoated with 50 μl collagen (AdvancedMatrix, Carlsbad, CA) as per a published method (movie link); be careful not to break the pellet, first gently resuspend the pellet from the bottom of the tube by taking a small amount of medium from the tube in the tip of the micropipettor and releasing it 'abruptly' to the side of the inner wall close to the tumor; pick up the pellet once it is in suspension with a 1 ml large orifice pipette tip.
11. Carefully remove the medium surrounding the pellet of nodules from the well with a micropipettor, without touching this pellet.
12. Add, drop-by-drop, 450 μl of collagen I prepared at 2000 Pa according to the manufacturer's instructions onto the nodules.
13. Keep the 4-well plate in the hood for 10 min.

14. Add 300 µl of H14 cell culture medium against the inner side of the well in order to avoid damaging the macrotumor.
15. Examine the macrotumors after 30 minutes and 24 h macroscopically to confirm integrity.
16. When ready for microscopy analysis involving staining, the cell culture medium is removed carefully and macrotumors are incubated in 4% paraformaldehyde (Santa Cruz; Dallas, TX) for 24 h in the fridge.
17. The pellets are given to the tissue core for paraffin embedding and tissue sectioning followed by H&E staining with or without immunohistochemistry with antibodies of interest.

Note: As an alternative, the small tumors can be prepared in collagen I and released with collagenase (see reference 15 for complete details) before being spun down and covered with collagen I as described in B).

C. Procedure for the Generation of Mixed Macrotumors with of IDC T4-2 Cells and DCIS S2 Cells Detailed protocols to handle the HMT3522 S2 cells and to prepare collagen I and do the thin-coating with collagen I on the cell culture surface are published[15].

1. Prepare S2 and T4 nodules (as in Section A)
2. [steps 2 and 3 are optional] Add a vital dye to the solution containing nodules and incubate for 30 min at 37° C.; CellMask™ Green Plasma Membrane Stain (50 µg/ml; ThermoFisher Scientific) was used for S2 nodules and DiI (50 µg/ml; ThermoFisher Scientific) was used for T4-2 nodules.
3. Wash the nodules three times with 300 µl H14 cell culture medium with a centrifugation step at 350 g for 5 min, between each wash.
4. Add 10 µl of fibronectin (100 µg/ml) and move the pellet up-and-down with a micropipettor and a 20 µl tip once or twice.
5. Let the solution stand for 1 min in the cell culture hood.
6. Add 90 µl of cell culture medium slowly against the inner wall of the Eppendorf tube
7. Keep the tube(s) at 37° C. for 20 min.
8. Spin down at 300 g for 1 min
9. Resuspend the nodules carefully in H14 medium; 0.5 ml for each group of six wells.
10. The nodules can be mixed in two different manners
    a. For controls (T4 or S2 nodules alone): Transfer 0.5 ml prelabeled T4 or S2 nodules into an microcentrifuge tube and spin down at 300 g for 1 min and proceed as in section B or steps 11 and on, below).
    b. Direct mixing of nodules: Transfer 0.25 ml prelabeled T4 and then 0.25 ml prelabeled S2 nodules to a microcentrifuge tube, mix gently once or twice with a micropipettor and a 1 ml tip, spin down at 300 g for 1 min and proceed as in section B or steps 11 and on, below).
    c. Step-wise centrifugation:
        i. Transfer 0.25 ml of prelabeled T4 nodules to a microcentrifuge tube.
        ii. Spin down at 300 g for 1 min and aspirate the medium.
        iii. Add slowly, against the inner wall of the tube, 0.25 ml prelabeled S2 nodules so that they are on top of the pellet of T4-2 nodules.
        iv. Spin down at 300 g for 1 min and aspirate the medium.
11. For the rest of the protocol see section B 8-17

D. Procedure for Generation of Macrotumors by Stacking with Paper-Scaffold

1. Laser cut cellulose acetate-based membranes (Sartorius stedim, Goettingen Germany) to 1.0 cm² scaffolds with holes micromachined at an average diameter of ~80 µm and density of ~4 pores/mm² using a laser engraver system (Universal Laser Systems, Inc., Scottsdale, AZ).
2. Sterilize the membranes under UltraViolet light in the cell culture hood for 2 h prior to cell culture.
3. Precoat a well of a 4-well plate with 50 µl collagen I at 2,000 Pa (Young's modulus).
4. Dip a cellulose acetate strip into a collagen I solution at 2,000 Pa (kept on ice) for five seconds and place it onto the collagen precoated well.
5. Transfer 0.5 ml (from 10-day standard 3D culture in six wells of a 4-well plate) T4-2 nodules, pre-incubated with fibronectin and labeled with DiI (see Section C, steps 1-9), to a microcentrifuge tube.
6. Spin down at 300 g for 1 min and aspirate the medium.
7. Add 200 µl of medium slowly against the inside wall of the tube.
8. Transfer the pellet of nodules by slowly aspirating it into a 1 ml large-bore pipette tip and depositing it gently onto the collagen I-coated paper.
9. Remove the excess medium in the well by aspirating it with a micropipettor with a 200 µl pipette tip.
10. Add 400 µl of collagen I (2,000 Pa) drop-by-drop onto the pellet of nodules.
11. Keep the plate in the cell culture hood for 10 min.
12. Prewet a paper-scaffold with collagen I as in step 2 and place it onto the layer of collagen-embedded nodules in the well but at an angle so that there is a corner easily accessible to peel off part of the tumor when necessary (see Supplementary FIG. 5a).
13. Repeat Steps 3 to 9.
14. Prewet a third paper-scaffold with collagen I as in step 2 and place it at an angle onto the nodules with collagen I from the second scaffold.
15. Repeat Steps 3 to 9.
16. Add 300 µl of H14 medium carefully to the side of the paper-scaffold stack and place the cell culture vessel in the incubator.
17. Examine the cell culture after 30 min and 24 h macroscopically to assess the integrity of the macrotumor.
18. When the culture is done, use a 200 µl pipette tip to circle around the inside of the well in order to loosen the paper stack from the well.
19. Place the cover of a 100 mm Petri dish onto the well and turn the stack upside down.
20. Tap the bottom of the well to allow the stack to slide onto the cover of the Petri dish.
21. Use two tweezers to separate the papers from the stack one by one. One tweezer is used for gripping the scaffold to peel off a tumor portion while the other tweezer is used for holding the other scaffold(s) underneath.

The invention claimed is:

1. A composition comprising a multilayer stacking for culturing macrotumors, wherein the multilayer stacking comprises a plurality of cell culture-amenable substrates and a plurality of cell pellets comprising a plurality of microtumor nodules of cancer cells, wherein the cell culture-amenable substrates and the cell pellets are stacked alternatively and are embedded in one or more extracellular matrices, wherein each substrate is separable and has a plurality of micro-machined holes with a diameter of 60-100 µm, which enable the formation of macrotumors with a diameter of 0.5 cm or more, wherein the density of the micro-machined holes on each substrate is 2-8 holes/cm², and wherein each substrate and cell pellet is pre-coated with one or more extracellular matrices.

2. The composition of claim 1, wherein the multilayer stacking comprises 2-4 cell culture-amenable substrates.

3. The composition of claim 1, wherein said cell culture-amenable substrates comprise a polymeric material.

4. The composition of claim 1, wherein the polymeric material is selected from cellulose acetate, polystyrene, polyurethane, polytetrafluoroethylene (PTFE), polyvinylchloride, polycarbonate, SU-8, or any combination thereof.

5. The composition of claim 1, wherein the one or more extracellular matrices of the multilayer stacking have has a stiffness of 500-8,000 Pa as measured by indentation of unconstrained samples.

6. The composition of claim 1, wherein the one or more extracellular matrices are selected from collagen I, fibronectin, collagen III, collagen IV, laminins, hyaluronic acid, heparan sulfate proteoglycan, or a combination thereof.

7. The composition of claim 1, wherein the extracellular matrices used to pre-coat the culture amenable substrate and the cell pellet can be the same or different.

8. The composition of claim 1, wherein the macrotumor size is 0.5 cm to 1.5 cm.

9. A method of preparing a macrotumor, comprising:
a) providing a first cell pellet comprising a plurality of microtumor nodules of cancer cells and diameters of 50-800 μm, wherein the first pellet is pre-coated with one or more extracellular matrices;
b) providing a first cell culture-amenable substrate, wherein the first substrate has a plurality of micro-machined holes with a diameter of 60-100 μm, wherein the density of the micro-machined holes on each substrate is 2-8 holes/mm², and the first substrate is pre-coated with one or more extracellular matrices, and depositing the first cell pellet comprising a plurality of microtumor nodules onto the first cell culture-amenable substrate;
c) adding one or more extracellular matrices onto the first pellet deposited on the first substrate to allow the first cell pellet to be embedded by the extracellular matrix;
d) depositing on top of the extracellular matrix of the first cell pellet a second cell culture-amenable substrate, wherein the second substrate has a plurality of micro-machined holes with a diameter of 60-100 μm, wherein the density of the micro-machined holes on each substrate is 2-8 holes/mm², and the second substrate is pre-coated with one or more extracellular matrices, and placing a second cell pellet comprising a plurality of microtumor nodules onto the second cell culture-amenable substrate, wherein the second pellet is pre-coated with one or more extracellular matrices;
e) adding one or more extracellular matrices onto the second cell pellet deposited on the second substrate to allow the second cell pellet to be embedded by the extracellular matrix;
f) optionally repeating steps d)-e) to provide a total of 2-4 cell culture-amenable substrates, wherein each cell pellet comprising a plurality of microtumor nodules and each substrate are stacked alternatively; and
g) incubating the obtained multilayer stacking in a cell culture medium, wherein each cell culture-amenable substrate is separable, upon which a macrotumor with a diameter of 0.5 cm or more is formed.

10. The method of claim 9, wherein the microtumor nodules can be the same or different to provide homogeneous or heterogeneous macrotumors.

11. The method of claim 9, wherein the microtumor nodules are from cells representing different types of carcinomas.

12. The method of claim 9, wherein said one or more extracellular matrices is selected from collagen I, fibronectin, collagen III, collagen IV, laminins, hyaluronic acid, heparan sulfate proteoglycan, or a combination thereof.

13. The method of claim 9, wherein the extracellular matrices used to pre-coat the culture-amenable substrate and the cell pellet can be the same or different.

* * * * *